(12) United States Patent
Deshayes et al.

(10) Patent No.: US 10,463,587 B2
(45) Date of Patent: Nov. 5, 2019

(54) 10-HYDROXYSTEARIC ACID COMPOSITIONS

(71) Applicant: DSM IP Assets B.V., Heerlen (NL)

(72) Inventors: Cyrille Deshayes, Kaiseraugst (CH); Christine Mendrok-Edinger, Kaiseraugst (DE)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/092,555

(22) PCT Filed: Mar. 29, 2017

(86) PCT No.: PCT/EP2017/057425
§ 371 (c)(1),
(2) Date: Oct. 10, 2018

(87) PCT Pub. No.: WO2017/178236
PCT Pub. Date: Oct. 19, 2017

(65) Prior Publication Data
US 2019/0117539 A1 Apr. 25, 2019

(30) Foreign Application Priority Data
Apr. 13, 2016 (EP) .................... 16164997

(51) Int. Cl.
*A61K 8/365* (2006.01)
*A61Q 7/00* (2006.01)
*A61Q 19/00* (2006.01)
*A61K 8/06* (2006.01)
*A61K 8/34* (2006.01)
*A61K 8/368* (2006.01)
*A61Q 17/04* (2006.01)

(52) U.S. Cl.
CPC .............. *A61K 8/365* (2013.01); *A61K 8/062* (2013.01); *A61K 8/345* (2013.01); *A61K 8/368* (2013.01); *A61Q 7/00* (2013.01); *A61Q 19/00* (2013.01); *A61K 2800/49* (2013.01); *A61K 2800/524* (2013.01); *A61K 2800/5922* (2013.01); *A61Q 17/04* (2013.01)

(58) Field of Classification Search
None
See application file for complete search history.

(56) References Cited

U.S. PATENT DOCUMENTS

2012/0157528 A1 6/2012 Pehratovic et al.

FOREIGN PATENT DOCUMENTS

| EP | 2877445 A1 * | 6/2015 |
|----|-----|-----|
| JP | 2009-286739 | 12/2009 |
| WO | 2014/095255 | 6/2014 |
| WO | 2014/095257 | 6/2014 |
| WO | 2016/059169 | 4/2016 |

OTHER PUBLICATIONS

International Search Report for PCT/EP2017/057425 dated Jul. 6, 2017, 4 pages.
Masaki et al., "Non-aqueous composition for cleansing skin, preferably washing face with warm sensation, comprises non-polar oil, exothermic agent, hydroxyl stearic acid, nonionic surfactant and freshener", *WPI/Thomson*, vol. 2010, No. 1, Dec. 10, 2009, one (1) page.

* cited by examiner

*Primary Examiner* — Robert A Wax
*Assistant Examiner* — Randeep Singh
(74) *Attorney, Agent, or Firm* — Nixon & Vanderhye P.C.

(57) ABSTRACT

The present invention relates to topical compositions comprising 10-hydroxystearic acid or a salt thereof in combination with 12-hydroxystearic acid or a salt thereof. The present invention also relates to a method to retard or inhibit the recrystallization of 10-hydroxystearic acid or a salt thereof in a topical composition, said method comprising formulating 10-hydroxystearic acid or a salt thereof in the presence of 12-hydroxystearic acid or a salt thereof.

13 Claims, No Drawings

10-HYDROXYSTEARIC ACID COMPOSITIONS

This application is the U.S. national phase of International Application No. PCT/EP2017/057425 filed Mar. 29, 2017 which designated the U.S. and claims priority to EP Patent Application No. 16164997.5 filed Apr. 13, 2016, the entire contents of each of which are hereby incorporated by reference.

The present invention relates to topical compositions comprising 10-hydroxystearic acid or a salt thereof in combination with 12-hydroxystearic acid or a salt thereof. The present invention also relates to a method to retard or inhibit the recrystallisation of 10-hydroxystearic acid or a salt thereof in a topical composition, said method comprising formulating 10-hydroxystearic acid or a salt thereof in the presence of 12-hydroxystearic acid or a salt thereof.

Hydroxy fatty acids such as 10-hydroxystearic acid (CAS: 638-26-6) have been reported to have beneficial cosmetic effects in treating or preventing any symptoms caused by negative developments of the physiological homeostasis of healthy skin, as well as for the promotion of hair growth and protection from hair loss. However none of these compounds have been developed into commercial products because of difficulties in establishing product forms in which the active remains soluble over time and does not recrystallize upon storage.

Thus, there is an ongoing need to overcome the drawbacks of the prior art and to find a robust and stable emulsion system which allows the incorporation of 10-hydroxystearic acid without the formation of crystals upon storage.

Surprisingly it has been found that the recrystallization of 10-hydroxystearic acid can be significantly retarded or even inhibited by co-formulating it with 12-hydroxystearic acid or a salt thereof.

Thus, in a first embodiment the invention relates to topical compositions comprising 10-hydroxystearic acid or a salt thereof and 12-hydroxystearic acid or a salt thereof.

The amount of 10-hydroxystearic acid or a salt thereof in the topical compositions according to the invention is advantageously selected in the range of 0.001 to 5 wt.-%, preferably in the range of 0.01 to 3 wt.-%, most preferably in the range of 0.1 to 2 wt.-%, such as in particular in the range of 0.1 to 1.5 wt.-%, always based on the total weight of the composition.

The amount of 12-hydroxystearic acid or a salt thereof in the topical compositions according to the invention is advantageously selected in the range of 0.001 to 5 wt.-%, preferably in the range of 0.01 to 3 wt.-%, most preferably in the range of 0.1 to 2 wt.-%, such as in particular in the range of 0.1 to 1.5 wt.-%, always based on the total weight of the composition.

Preferably the ratio (molar) of 10-hydroxystearic acid or a salt thereof to 12-hydroxystearic acid or a salt thereof is selected in the range of 20:1 to 1:10, preferably in the range of 15:1 to 1:10, most preferably in the range of 10:1 to 1:1.

10-Hydroxystearic acid (synonym: 10-Hydroxyoctadecanoic acid, CAS: 638-26-6) can e.g. prepared as illustrated by G. Schroepfer in Biological Chemistry (1966), 241(22), 5441-7 and has the following formula:

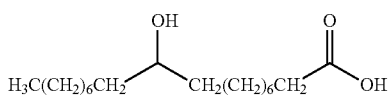

Both enantiomers may be used according to the present invention, and the preferred enantiomeric form is the (R)-10-hydroxystearic acid.

12-Hydroxystearic acid (synonym: 12-Hydroxyoctadecanoic acid, CAS: 106-14-9) is e.g. commercially available at Sigma-Aldrich respectively Alberdink Boley and has the following formula:

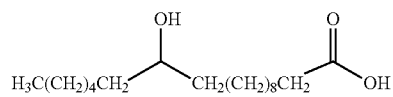

Preferably the 12-HYdroxystearic acid used according to the present invention is derived from castor oil by hydrogenation and hydrolysis and has a purity in the range of at least 80%, such as in the range of 80-85%.

The respective salts may be formed by reaction with an organic base, or an alkali or earth alkaline base resulting in the respective salt. Suitable bases which release a cosmetically acceptable cation that is not toxic to the skin and/or does not cause allergic reactions are well known to a person skilled in the art. Examples of organic salts are the respective ammonium and alkyl ammonium salts such as in particular the triethanolammonium salts. Preferred alkali or earth alkali salts are the respective lithium, sodium, potassium, magnesium or calcium salts such as in particular potassium and sodium salts.

The topical compositions according to the present invention are preferably free of isobutyl paraben, more preferably, however, the compositions are free of any paraben such as in particular free of methylparaben, ethylparaben, propylparaben, and butylparaben.

In another embodiment, the present invention relates to a method to retard or inhibit the re-crystallisation of 10-hydroxystearic acid or a salt thereof in a topical composition, said method comprising formulating 10-hydroxystearic acid or a salt thereof in the presence of 12-hydroxystearic acid or a salt thereof with all the preferences and definitions given above.

The term "topical composition" as used herein refers in particular to cosmetic compositions that can be topically applied to mammalian keratinous tissue such as e.g. human skin or hair, particularly human skin.

The term "cosmetic composition" as used in the present application refers to cosmetic compositions as defined under the heading "Kosmetika" in Römpp Lexikon Chemie, 10th edition 1997, Georg Thieme Verlag Stuttgart, New York as well as to cosmetic preparations as disclosed in A. Domsch, "Cosmetic Preparations", Verlag für chemische Industrie (ed. H. Ziolkowsky), 4$^{th}$ edition, 1992.

Preferably, the topical preparations according to the present invention are in the form of an emulsion or micro emulsion (in particular of O/W-type), PIT-emulsion, multiple emulsion (e. g. O/W/O-type and W/O/W) or pickering emulsion.

In all embodiments of the present invention the topical compositions according to the present invention are preferably emulsions or micro emulsion (in particular of O/W-type), PIT-emulsion, multiple emulsion (e. g. O/W/O-type and W/O/W) or pickering emulsion comprising an aqueous phase and an oily phase wherein the aqueous phase preferably constitutes at least 50 wt.-% and the oily phase preferably constitutes at least 10 wt.-% of the composition. More preferably the aqueous phase constitutes at least 60 wt.-% and the oily phase constitutes less than 40 wt.-%. In particular the aqueous phase constitutes at least 70 wt.-% and the oily phase constitutes less than 30 wt.-% of the total composition. Most preferably in all embodiments of the present invention, the amount of the aqueous phase is selected in the range of 70-90 wt.-% and the amount of the oily phase is selected in the range of 10-30 wt.-%, based on the total weight of the composition.

It is well understood, that the aqueous (water) phase and the oily phase together form the emulsion, wherein, however, minor amounts (up to 5 wt.-%) of remainder ingredients such as preservatives, active, fragrances, etc. may also be present which may be added to one of the phases or separately e.g. at end of the preparation which is well known to a person skilled in the art.

Particular suitable oil components and solvents to form the oily phase of the topical compositions according to the present invention encompass:

Ethanol; Triethylhexanoin; Glycols such as propylene glycol, propylene glycol dibenzoate, butylene glycol, pentylene glycol and PPG-15 ethoxydiglycol stearyl ether; Dialkylethers such as dicaprylyl ether, PPG-3 myristyl ether; Esters of saturated and/or unsaturated, branched and/or unbranched alkanecarboxylic acids having a chain length of 3 to 30 carbon atoms and saturated and/or unsaturated, branched and/or unbranched alcohols having a chain length of 3 to 30 carbon atoms, or from esters of aromatic carboxylic acids and saturated and/or unsaturated, branched and/or unbranched alcohols having a chain length of 3 to 30 C atoms such as e.g. isopropyl myristate, isopropyl palmitate, isopropyl oleate, n-butyl stearate, n-hexyl laurate, n-decyl oleate, isononyl isononanoate, 2-ethylhexyl palmitate, ethylhexyl benzoate, $C_{12-15}$ alkyl benzoate, 2-hexyl decyl stearate, oleyl oleate, erucyl oleate, erucyl erucate, propylene glycol dicaprylate/dicaprate, diisopropyl adipate, isoamyl laurate, octyldodecyl neopentanoate, di-$C_{12}$-$C_{13}$ alkyl tartrate and synthetic, semi-synthetic and natural mixtures of such esters such as e.g. jojoba oil; Carbonates such as dicaprylyl carbonate; Triglycerides such as caprylic/capric triglyceride, PEG-8 caprylic/capric triglycerides; Silicone oils; Straight or branched chain hydrocarbons having from 8-20 carbon atoms, such as decane, dodecane, tridecane, tetradecane, and $C_8$-20 isoparaffins; Natural oils and fats (including butters) derived from animal, vegetable, or mineral sources such as e.g. almond oil, apricot kernel oil, argan oil, avocado butter, avocado oil, cocoa butter (theobroma oil), camelina oil, canola oil, carrot seed oil, castor oil, citrus seed oil, coconut oil, corn oil, cottonseed oil, cucumber oil, egg oil, grapeseed oil, hemp seed oil, jojoba oil, lanolin oil, linseed oil, macadamia nut oil, meadowfoam seed oil, mineral oil, mink oil, olive oil, palm kernel oil, peach kernel oil, peanut oil, rapeseed oil, rose hip oil, safflower oil, sesame oil, shark liver oil, shea butter, soybean oil, sunflower seed oil, sweet almond oil, tallow (beef) oil, tallow (mutton) oil, turtle oil, vegetable oil, and wheat germ and as well as mixtures of these oil components and solvents.

Particularly suitable oil and solvent components to form the oil phase of the topical composition according to the present invention are isopropyl palmitate, caprylic/capric triglyceride, PPG-15 stearyl ether, butylene glycol, dicaprylyl carbonate, dicaprylyl ether, di-$C_{12}$-$C_{13}$ alkyl tartrate, diisopropyl adipate, triethylhexanoin, propylene glycol dicaprylate/dicaprate, isoamyl laurate, octyldodecyl neopentanoate, ethylhexyl benzoate, pentylene glycol, PEG-8 caprylic/capric triglycerides, propylene glycol dibenzoate, PPG-3 myristyl ether, ethoxydiglycol, $C_{12}$-15 alkyl benzoate and ethanol as well as mixtures thereof.

Preferably the topical compositions according to the present invention are O/W emulsions.

In a preferred embodiment, these O/W emulsions contain at least one O/W- or Si/W-emulsifier selected from the list consisting of sodium cetearyl sulfate, glyceryl stearate citrate, glyceryl stearate, stearic acid, salts of stearic acid, polyglyceryl-3-methylglycosedistearate, methyl glucose sesquistearate, sodiumcetearylsulfat, sodium glyceryl oleate phosphate, hydrogenated vegetable glycerides, sorbitan oleate, sorbitan sesquioleate, sorbitan isostearate, sorbitan trioleate, cetearyl glucoside, cetearyl olivate, lauryl glucoside, decyl glucoside, sodium stearoyl glutamate, sucrose polystearate, hydrated polyisobuten, phosphate ester emulsifiers such as in particular $C_{8-10}$ alkyl ethyl phosphate, $C_{9-15}$ alkyl phosphate, ceteareth-2 phosphate, ceteareth-5 phosphate, ceteth-8 phosphate, ceteth-10 phosphate, cetyl phosphate, $C_{6-10}$ pareth-4 phosphate, $C_{12-15}$ pareth-2 phosphate, $C_{12-15}$ pareth-3 phosphate, DEA-ceteareth-2 phosphate, DEA-cetyl phosphate, DEA-oleth-3 phosphate, potassium cetyl phosphate, deceth-4 phosphate, deceth-6 phosphate and trilaureth-4 phosphate, polyethylene glycol alkyl ether (PEG-ether) such as in particular steareth-2 and steareth-21, polyethylene glycol fatty acid esters (PEG-esters) such as in particular PEG-40 stearate and PEG-100 stearate, block polymers of polyethylene glycol and polypropylene glycol such as in particular PPG-1-PEG-9 lauryl glycol ether, PPG-1-PEG-9 lauryl glycol ether, PEG/PPG-18/18 dimethicone and cetyl PEG/PPG-10/1 dimethicone as well as synthetic polymers with emulsifying properties such as PVP eicosene copolymer, acrylates/$C_{10-30}$ alkyl acrylate crosspolymer, as well as mixtures of these emulsifiers.

The at least one O/W, respectively Si/W emulsifier is preferably used in an amount (total) of 0.5 to 10 wt.-%, in particular in the range of 0.5 to 6 wt.-%, such as more in particular in the range of 0.5 to 5 wt.-%, such as most in particular in the range of 0.5 to 4 wt.-%, based on the total weight of the composition.

Particular suitable O/W emulsifier to be used in the topical compositions according to the invention encompass sodium cetearyl sulfate (Lanette E), glyceryl stearate citrate (Imwitor) and is potassium cetyl phosphate (Amphisol® K). Most preferred in all embodiments of the present invention is potassium cetyl phosphate (Amphisol® K). e.g. commercially available as at DSM Nutritional Products Ltd Kaiseraugst.

In an advantageous embodiment, the invention relates to topical compositions with all the definitions and preferences given herein in the form of O/W emulsions comprising an oily phase dispersed in an aqueous phase in the presence of an O/W emulsifier wherein the O/W emulsifier is potassium cetyl phosphate.

The topical compositions according to the present invention preferably contain additionally a co-emulsifier. Particular preferred co-emulsifiers according to the present invention are nonionic solid fatty alcohols having from 12 to 22 carbon atoms as well as mixtures thereof such as preferably lauryl alcohol, myristyl alcohol, pentadecyl alcohol, cetyl alcohol, heptadecyl alcohol, stearyl alcohol, isostearyl alcohol, palmitoleyl alcohol as well as mixtures thereof. Particular preferred co-emulsifiers are selected from the group consisting of behenyl alcohol which is e.g. commercially available as Lanette 22 from BASF, cetyl alcohol which is e.g. commercially available as Lanette 16 from BASF, glyceryl stearate which is e.g. commercially available as Cithrol GMS 40 from Croda or Cutina GMS from BASF and cetearyl alcohol (i.e. a mixture of cetyl- and stearyl alcohol), which is e.g. commercially available as Lanette® O from BASF, as well as mixtures thereof.

The (total) amount of co-emulsifier in the topical compositions according to the present invention is preferably selected in the range of 0.1 to 20 wt.-%, more preferably in the range of 0.5 to 10 wt.-%, most preferably in the range of 1 to 5 wt.-%, based on the total weight of the composition.

The aqueous phase advantageously consists essentially of water, a moisturizer and a thickener. Suitable thickeners encompass e.g. xanthan gum e.g. available as Keltrol CG-RD, guar-gum, alginate, polyacrylates, polyquaternium, silicone-based polymers, carbomers, acrylates/C10-30 alkyl acrylates copolymers, hydroxyethylcellulose, ammonium acryloyldimethyltaurate/VP copolymer as well as other acryloyldimethyl taurate copolymers. Preferred thickeners are xanthan gum or acrylates/$C_{10-30}$ alkyl acrylates copolymers or polyacrylic acid (INCI: Carbomer).

According to the invention xanthan gum is preferably used in low concentrations such as e.g. in concentrations selected in the range of 0.05-1 wt.-%, preferably in the range of 0.05-0.3 wt.-%, based on the total weight of the topical composition.

According to the invention acrylates/$C_{10-30}$ alkyl acrylates are preferably used in low concentrations such as e.g. in concentrations selected in the range of 0.05-1 wt.-%, preferably in the range of 0.05-0.3 wt.-%, based on the total weight of the topical composition.

According to the invention polyacrylic acid is preferably used in low concentrations such as e.g. in concentrations selected in the range of 0.05-1 wt.-%, preferably in the range of 0.05-0.3 wt.-%, based on the total weight of the topical composition.

A particularly suitable moisturizer is glycerine, but not limited to. Other suitable moisturizers encompass saccharide isomerate e.g. available as Pentavitin®, penthylene glycol e.g. available as Hydrolite®, propylene glycol, butylene glycol and urea, as well as mixtures thereof.

According to the invention glycerine is preferably used in low concentrations such as in concentrations selected in the range of 0.5-10 wt.-%, more preferably in the range of 1-6 wt.-%, based on the total weight of the topical composition.

Particular suitable preservatives to be used in the topical compositions according to the invention are selected from the group consisting of phenoxyethanol, ethylhexyl glycerine, potassium sorbate and sodium benzoate as well as mixtures thereof.

According to the invention the preservative (total amount) is preferably used in low concentrations such as in concentrations selected in the range of 0.1-3 wt.-%, more preferably in the range of 0.5-2 wt.-%, most preferably in the range of 0.5 to 1 wt.-%, based on the total weight of the topical composition.

Topical compositions in accordance with the invention can be in the form of a liquid, lotion, a thickened lotion, a gel, a cream, a milk, an ointment or paste, and can be optionally be packaged as an aerosol and can be provided in the form of a mousse such as an aerosol mousse, a foam or a spray foam, a spray, a stick.

The topical compositions according to the invention may optionally be combined with further cosmetically active ingredients such as ingredients for skin lightening; tanning prevention; treatment of hyperpigmentation and/or cellulite; preventing or reducing acne, wrinkles, lines, atrophy and/or inflammation; slimming (e.g. phytanic acid), firming, moisturizing, energizing, self-tanning, soothing, as well as agents to improve elasticity and skin barrier. It's well known to a person skilled in the art that the cosmetically active ingredients useful herein can in some instances provide more than one benefit or operate via more than one mode of action.

If present, the additional cosmetically active ingredient is typically included in an amount of at least 0.001 wt. %, based on the total weight of the topical preparation. Generally, an amount of about 0.001 wt. % to about 30 wt. %, preferably from about 0.001 wt. % to about 10 wt. %, based on the total weight of the topical composition of an additional cosmetically active agent is used.

The topical cosmetic compositions of the invention can also contain usual cosmetic adjuvants and additives, such as preservatives/antioxidants, fatty substances/oils, water, organic solvents, silicones, thickeners, softeners, emulsifiers, sunscreens, antifoaming agents, aesthetic components such as fragrances, surfactants, fillers, sequestering agents, chelating agents, anionic, cationic, nonionic or amphoteric polymers or mixtures thereof, propellants, acidifying or basifying agents, dyes, colorings/colorants, abrasives, absorbents, essential oils, skin sensates, astringents, pigments or nanopigments, e.g. those suited for providing a photoprotective effect by physically blocking out ultraviolet radiation, or any other usual cosmetic adjuvant or additive usually formulated into cosmetic compositions.

Active ingredients as well as cosmetic adjuvants and additives commonly used in the skin care industry and which are suitable for their use in the compositions of the present invention are e.g. described in the CTFA Cosmetic Ingredient Handbook, Second Edition (1992) without being limited thereto.

The necessary amounts of the active ingredients as well as cosmetic adjuvants and additives can—based on the desired product—easily be chosen by a skilled person in this field and will be illustrated in the examples, without being limited hereto.

Of course, one skilled in this art will take care to select the above mentioned optional additional compound or compounds and/or their amounts such that the advantageous properties intrinsically associated with the combination in accordance with the invention are not, or not substantially, detrimentally affected by the envisaged addition or additions.

Suitable UV-filter substance to be incorporated into the topical compositions according to the present invention are conventional UVA and/or UVB and/or broad spectrum UV-filter substances known to be added into topical compositions such as cosmetic or dermatological sun care products. Such UV-filter substances comprise all groups which absorb light in the range of wavelengths 400 nm to 320 nm (UVA) and 320 nm to 280 nm (UVB) or of even shorter wavelengths (UVC) and which are or can be used as cosmetically acceptable UV-filter substances. Such UV-filter substances are e.g. listed in the CTFA Cosmetic ingredient Handbook or "The Encyclopedia of Ultraviolet Filters" (ISBN: 978-1-932633-25-2) by Nadim A. Shaath.

Suitable UV-filter substances may be organic or inorganic compounds. Exemplary organic UV-filter substances encompass e.g. acrylates such as e.g. 2-ethylhexyl 2-cyano-3,3-diphenylacrylate (octocrylene, PARSOL® 340), ethyl 2-cyano-3,3-diphenylacrylate; Camphor derivatives such as e.g. 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, terephthalylidene dicamphor sulfonic acid (Mexoryl® SX); Cinnamate derivatives such as e.g. ethylhexyl methoxycinnamate (PARSOL® MCX), ethoxyethyl methoxycinnamate, isoamyl methoxycinnamate as well as cinnamic acid derivatives bond to siloxanes; p-Aminobenzoic acid derivatives such as e.g. p-aminobenzoic acid, 2-ethylhexyl p-dimethyl-aminobenzoate, N-oxypropylenated ethyl p-aminobenzoate, glyceryl p-aminobenzoate; Benzophenones such as e.g. benzophenone-3, benzophenone-4,2,2',4,4'-tetrahydroxy-benzophenone, 2,2'-dihydroxy-4,4'-dimethoxybenzophenone; Esters of benzalmalonic acid such as e.g. di-(2-ethylhexyl) 4-methoxybenzalmalonate; Organosiloxane compounds carrying chromophore groups such as e.g. polysilicones-15 (PARSOL® SLX), drometrizole trisiloxane (Mexoryl® XL); Imidazole derivatives such as e.g. 2-phenyl benzimidazole sulfonic acid (PARSOL® HS) and salts thereof such as e.g. sodium- or potassium salts, ammonium salts, morpholine salts, salts of primary, sec. and tert. amines like monoethanolamine salts, diethanolamine salts; Salicylate derivatives such as e.g. isopropylbenzyl salicylate, benzyl salicylate, butyl salicylate, ethylhexyl salicylate (PARSOL® EHS, Neo Heliopan® OS), isooctyl salicylate or homomenthyl salicylate (homosalate, PARSOL® HMS, Neo Heliopan® HMS); Triazine derivatives such as e.g. ethylhexyl triazone (Uvinul® T-150), diethylhexyl butamido triazone (Uvasorb® HEB), bis-ethylhexyloxyphenol methoxyphenyl triazine (Tinosorb® S), 2,4,6-Tris([1,1'-Biphenyl]-4-yl)-1,3, 5-Triazine (Tris Biphenyl Triazine, Tinosorb A2B); Benzotriazole derivatives such as e.g. 2,2'-methylene-bis-(6-(2H-benzotriazole-2-yl)-4-(1,1,3,3,-tetramethylbutyl)-phenol (Tinosorb® M); Encapsulated UV-filters such as e.g. encapsulated ethylhexyl methoxycinnamate (Eusolex® UV-pearls) or microcapsules loaded with UV-filters as e.g. dislosed in EP 1471995; Dibenzoylmethane derivatives such as e.g. 4-tert.-butyl-4'-methoxydibenzoyl-methane (PARSOL® 1789), dimethoxydibenzoylmethane, isopropyldibenzoylmethane; Phenylene-1,4-bis-benzimidazolsulfonic acids or salts such as e.g. 2,2-(1,4-phenylene)bis-(1H-benzimidazol-4,6-disulfonic acid) (Neoheliopan AP); Amino substituted hydroxybenzophenones such as e.g. 2-(4-diethylamino-2-hydroxy-benzoyl)-benzoic acid hexylester (Aminobenzophenon, Uvinul® A Plus); Benzoxazol-derivatives such as e.g. 2,4-bis-[5-1(dimethylpropyl)benzoxazol-2-yl-(4-phenyl)-imino]-6-(2-ethylhexyl)-imino-1,3,5-triazine (Uvasorb® K2A); Inorganic UV-filter substances encompass pigments such as e.g. microparticulated Zink oxide or Titanium dioxide (e.g. commercially available as PARSOL® TX) The term "microparticulated" refers to a particle size from about 5 nm to about 200 nm, particularly from about 15 nm to about 100 nm. The particles may also be coated by other metal oxides such as e.g. aluminum or zirconium oxides or by organic coatings such as e.g. polyols, methicone, aluminum stearate, alkyl silane. Such coatings are well known in the art.

In order to enhance the photostability of sun care products it may be desirable to add a photostabilizer. Exemplary photostabilizers known to a skilled person in the art encompass e.g. 3,3-diphenylacrylate derivatives such as e.g. octocrylene (PARSOL® 340) or Polyester-8 (Polycrylene®); Benzylidene camphor derivatives such as e.g. 4-methyl benzylidene camphor (PARSOL® 5000); Benzalmalonate derivatives such as e.g. polysilicones-15 (PARSOL® SLX) or diethylhexyl syringylidene malonate (Oxynex ST liquid); Dialkyl naphthalates such as diethylhexyl naphthalate (Corapan TQ) without being limited thereto. An overview on further stabilizers is e.g. given in 'SPF Boosters & Photostability of Ultraviolet Filters', HAPPI, October 2007, p. 77-83 which is included herein by reference. The photostabilizers are generally used in an amount of 0.05 to 10 wt.-% with respect to the total weigh of the topical composition.

Generally, the amount of each UV-filter substance in the topical compositions according to the invention is selected in the range of about 0.1 to 10 wt.-%, preferably in the range of about 0.2 to 10 wt.-%, most preferably in the range of about 0.5 to 10 wt.-%, based on the total weight of the topical composition.

The total amount of UVA-filter substance(s), in particular of butyl methoxydibenzoylmethane, in the topical compositions according to the invention is preferable selected in the range of about 0.5 to 8 wt.-%, in particular in the range of about 1 to 6 wt.-%, most particular in the range of about 1 to 5 wt.-%, based on the total weight of the topical composition.

The total amount of UV-filter substances in the topical compositions according to the invention is preferably in the range of about 1 to 40 wt.-%, preferably in the range of about 5 to 30 wt.-%, in particular in the range of 8 to 30 wt.-%, based on the total weight of the topical composition.

Preferred UVB-filter substances to be incorporated into the topical compositions according to the present invention encompass polysilicones-15, phenylbenzimidazol sulfonic acid, octocrylene, ethylhexyl methoxycinnamate, ethyl hexylsalicylate and/or homosalate.

Preferred broadband UV-filter substances to be incorporated into the topical compositions according to the present invention encompass unsymmetrical s-triazine derivatives such 2,4-Bis-{[4-(2-ethyl-hexyloxy)-2-hydroxy]-phenyl}-6-(4-methoxyphenyl)-1,3,5-triazine or 2,4,6-Tris([1,1'-Biphenyl]-4-yl)-1,3,5-Triazine (Tris Biphenyl Triazine, Tinosorb A2B), certain benzophenones such as e.g. 2-Hydroxy-4-methoxy-benzophenon, 2,2'-Methylen-bis-(6-(2H-benzotriazol-2-yl)-4-(1,1,3,3-tetramethyl-butyl)-phenol), and/or titanium dioxide.

The preferred UVA-filter substance to be incorporated into the topical compositions according to the present invention is butyl methoxydibenzoylmethane. Preferably, butyl methoxydibenzoylmethane is the only UVA-filter substance in the topical compositions according to the invention.

In a particular preferred embodiment, the composition comprise at least one UV-filter substance selected from the group consisting of butyl methoxydibenzoylmethane, octocrylene, homosalate and ethylhexyl salate as well as mixtures thereof. In a particular advantageous embodiment all of butyl methoxydibenzoylmethane, octocrylene, homosalate and ethylhexyl salate are present in the compositions according to the present invention.

The topical compositions according to the present invention preferably have a viscosity of at least 1000 mPs (determined by TA Instruments AR 550, Shear rate $1s^{-1}$, 25° C., plate SST ST 40 mm), preferably in the range of 2000-15000 mPas such as in the range of 5000-13000 mPas.

The topical compositions according to the invention have a pH in the range of 3-10, preferably in the range of pH of 4-8, most preferred in the range of pH 4-7.

The following examples are provided to further illustrate the compositions and effects of the present invention. These examples are illustrative only and are not intended to limit the scope of the invention in any way.

EXAMPLE 1

Various formulations using no (Reference 1) or different fatty acids as additive (stearic acid (Reference 2), oleic acid (Reference 3) and 12-Hydroxystearic Acid (Invention)) have been prepared as outlined in Table 1. Initially, no crystals have been observed in any of the formulations by microscopy analysis. Then the formulations have been stored at room temperature and repeatedly been microscopically analyzed for re-crystallization of 10-hydroxystearic acid up to 3 months. The results thereof are outlined in Table 2.

TABLE 1

|   | INCI | Ref-1 1 | Ref-2 S-1 | Ref-2 S-2 | Ref-3 O-1 | Invention I-1 | Invention I-2 | Invention I-3 |
|---|---|---|---|---|---|---|---|---|
| A | Butyl Methoxydibenzoyl Methane | 3.0 | 3.0 | 3.0 | 3.0 | 3.0 | 3.0 | 3.0 |
|   | Octocrylene | 2.7 | 2.7 | 2.7 | 2.7 | 2.7 | 2.7 | 2.7 |
|   | Homosalate | 5.0 | 5.0 | 5.0 | 5.0 | 5.0 | 5.0 | 5.0 |
|   | Ethylhexyl Salicylate | 5.0 | 5.0 | 5.0 | 5.0 | 5.0 | 5.0 | 5.0 |
|   | C12-15 Alkyl Benzoate | 5.0 | 5.0 | 5.0 | 4.0 | 5.0 | 5.0 | 5.0 |
|   | Cetearyl Alcohol | 2.0 | 2.0 | 2.0 | 2.0 | 2.0 | 2.0 | 2.0 |
|   | Behenyl alcohol | 1.0 | 1.0 | 1.0 | 1.0 | 1.0 | 1.0 | 1.0 |
|   | BHT | 0.1 | 0.1 | 0.1 | 0.1 | 0.1 | 0.1 | 0.1 |
|   | Acrylates/C10-30 Alkyl Acrylate Crosspolymer | 0.1 | 0.1 | 0.1 | 0.1 | 0.1 | 0.1 | 0.1 |
|   | Potassium Cetyl Phosphate | 2.0 | 2.0 | 2.0 | 2.0 | 2.0 | 2.0 | 2.0 |
|   | 10-Hydroxystearic Acid | 1.0 | 0.5 | 0.9 | 1.0 | 0.5 | 0.9 | 1 |
|   | Stearic Acid |   | 0.5 | 0.1 |   |   |   |   |
|   | Oleic Acid |   |   |   | 1.0 |   |   |   |
|   | 12-Hydroxystearic Acid |   |   |   |   | 0.5 | 0.1 | 1 |
| B | Xanthan Gum | 0.2 | 0.2 | 0.2 | 0.2 | 0.2 | 0.2 | 0.2 |
|   | Disodium EDTA | 0.1 | 0.1 | 0.1 | 0.1 | 0.1 | 0.1 | 0.1 |
|   | Butylene Glycol | 2.0 | 2.0 | 2.0 | 2.0 | 2.0 | 2.0 | 2.0 |
|   | Sodium Hydroxide | 0.1 | 0.1 | 0.1 | 0.1 | 0.1 | 0.1 | 0.1 |
|   | Aqua |   |   |   | Ad 100 |   |   |   |
| C | Phenoxyethanol; Ethylhexylglycerine | 1.0 | 1.0 | 1.0 | 1.0 | 1.0 | 1.0 | 1.0 |
|   | microscopy aspect crystallization after | 2 weeks | | | 6 weeks | No crystals after 3 months | | |

The invention claimed is:

1. A method to retard or inhibit the re-crystallisation of 10-hydroxystearic acid or a salt thereof in a topical composition, wherein the method comprises formulating 10-hydroxystearic acid (10-HSA) or a salt thereof in the presence of 12-hydroxystearic acid (12-HSA) or a salt thereof at a molar ratio of the 10-HSA or salt thereof to the 12-HSA or salt thereof in an amount of 10:1 to 1:1.

2. The method claim 1, wherein the 10-HSA or salt thereof is present in an amount within a range of 0.001 to 5 wt.-%, based on total weight of the topical composition.

3. The method according to claim 1, wherein the 12-HSA or salt thereof is present in an amount within a range of 0.001 to 5 wt.-%, based on total weight of the topical composition.

4. The method according to claim 1, wherein the 10-HSA is (R)-10-hydroxystearic acid.

5. The method according to claim 1, wherein the 12-HSA is derived from castor oil.

6. The method according to claim 1, which comprises providing the topical composition as an O/W emulsion comprising an aqueous phase and an oily phase and at least one O/W or Si/W-emulsifier.

7. The method according to claim 6, wherein the aqueous phase comprises at least 50 wt.-% of the O/W-emulsion and the oily phase comprises at least 10 wt.-% of the O/W-emulsion, each based on total weight of the topical composition.

8. The method according to claim 6, wherein the at least one O/W emulsifier is potassium cetyl phosphate.

9. The method according to claim 6, wherein the at least one O/W or Si/W emulsifier is present in an amount of 0.5 to 10 wt. %, based on total weight of the topical composition.

10. The method according to claim 1, which includes including in the topical composition a co-emulsifier selected from the group consisting of nonionic solid fatty alcohols having from 12 to 22 carbon atoms and mixtures thereof.

11. The method according to claim 10, wherein the co-emulsifier is present in an amount within a range of 0.1 to 20 wt.-%, based on total weight of the composition.

12. The method according to claim 10, wherein the co-emulsifier is selected from the group consisting of cetyl alcohol, behenyl alcohol, glyceryl stearate, cetearyl alcohol and mixtures thereof.

13. The method according to claim 1, which comprises including in the composition at least one preservative selected from the group consisting of phenoxyethanol, ethylhexyl glycerine, potassium sorbate, sodium benzoate and mixtures thereof.

* * * * *